(12) United States Patent
Smith

(10) Patent No.: US 8,518,012 B2
(45) Date of Patent: Aug. 27, 2013

(54) DEVICE AND METHOD FOR RECTAL LAVAGE

(75) Inventor: Alan Smith, Kent (GB)

(73) Assignee: Intermark Medical Innovations Ltd., Kent (GB)

(*) Notice: Subject to any disclaimer, the term of this patent is extended or adjusted under 35 U.S.C. 154(b) by 2036 days.

(21) Appl. No.: 10/879,776

(22) Filed: Jun. 29, 2004

(65) Prior Publication Data

US 2005/0004533 A1    Jan. 6, 2005

(51) Int. Cl.
*A61M 31/00*    (2006.01)
*A61M 1/00*    (2006.01)

(52) U.S. Cl.
USPC ............ 604/514; 604/317; 604/319; 604/275; 604/27

(58) Field of Classification Search
USPC ................ 604/317, 319, 275, 514, 27, 73
See application file for complete search history.

(56) References Cited

U.S. PATENT DOCUMENTS

| | | |
|---|---|---|
| 1,591,410 A | 7/1926 | Spang |
| 1,942,422 A | 1/1934 | Hanna ........................ 128/241 |
| 5,443,445 A | 8/1995 | Peters |

FOREIGN PATENT DOCUMENTS

| | | |
|---|---|---|
| EP | 0 084 696 | 8/1983 |
| EP | 1 262 205 | 12/2002 |
| GB | 110 818 | 11/1917 |
| GB | 2 375 964 | 12/2002 |

OTHER PUBLICATIONS

Website screen of "A4050 'Colo-Shower' by Sapimed SpA of Italy".

*Primary Examiner* — Jacqueline F. Stephens
(74) *Attorney, Agent, or Firm* — Nields, Lemack & Frame, LLC

(57) ABSTRACT

The device for rectal lavage includes a generally rigid tubular body (10) having a relatively flexible tapered front end nozzle portion (12) for insertion into the anus (50) of a patient. A port (14) is provided for the insertion of an irrigation hose (16) into the device, which passes through a nozzle opening (18). At least one drain hole (20) is positioned in said nozzle (12), spaced from said opening (18), for the passage of irrigated fecal matter from the rectum (52) into the hollow interior (24) of said tubular body (10). A discharge outlet (22) member from the hollow interior (24) of said tubular body (10) for the discharge of irrigated fecal matter from the device. In the method, the device is inserted into the anus (50) of the patient, the irrigation hose (16) is fed through the device into the rectum (52) of the patient, irrigation fluid is passed through the irrigation hose (16) and irrigated fecal matter is allowed to pass through said drain holes (20) into the hollow interior (24) of said tubular body (10) and is discharged therefrom through said discharge outlet (22).

26 Claims, 4 Drawing Sheets

DEVICE AND METHOD FOR RECTAL LAVAGE

FIELD OF THE INVENTION

This invention relates to a device for rectal lavage, and to a method for using such a device, particularly for patients undergoing bowel surgery.

BACKGROUND OF THE INVENTION

Prior to and during colorectal surgery it is frequently necessary to lavage the rectum and distal colon either with an irrigation solution, a topical preparation, or both. It is however difficult to efficiently lavage the entire area, particularly when it is necessary to lavage the distal colon, and it is also difficult to contain and hygienically drain the waste fluid.

The most common known method uses a proctoscope inserted into the anal canal of the patient, through which lavage solution is injected into the rectum using a syringe. However, the proctoscope requires the use of an obturator for insertion which is then removed, leaving an unsealed opening and no means of containing the outflow of lavage fluid. It is thus difficult to contain fluid inside the patient for an adequate lavage, and there is no sealed or closed means of collecting draining fluid. Furthermore, use of a syringe limits the capacity to direct lavage fluid inside the patient.

The limitations of using a syringe can be overcome by using another known method, that of inserting a catheter or similar through the proctoscope and advancing it through the rectum and along the distal colon. This provides the capacity to direct lavage fluid, but not contain or drain it.

Another known method uses the A4050 "Colo-shower" available from SAPIMED SpA, Alessandria, Italy. The proctoscope is inserted using an obturator, the obturator is withdrawn and a plug with a sealing means inserted in the distal end of the proctoscope. A catheter is fed through the sealing means and into the patient as described above. Fluid drains through an outlet port into a receptacle provided by the user. Although the fluid outflow is restricted, it is not possible to completely contain the fluid in the patient, and the diameter of the outlet port is very narrow and may easily block.

We are aware that U.S. Pat. No. 5,443,445 (Peters et al./ Clinical Product Development Limited) describes an intra-operative colon irrigation system which includes a device having a tubular body with a forward end formed by a dome-shaped nozzle to prevent intussusception of the bowel, and a side tube including an outlet for the discharge of fecal matter from the device. A port is located at the other end of the tubular body, for the insertion of an ultrasonic device or for the injection of water or air under pressure.

SUMMARY OF THE INVENTION

It is an object of the present invention to provide a means of efficiently lavaging the rectum and optionally an extended length of the distal colon.

It is another object of the invention to provide a device for rectal lavage which does not require the use of an obturator for its insertion, but yet can be inserted in an atraumatic manner.

It is also a preferred object of the present invention to provide a means of containing fluid temporarily in the rectum and distal colon when necessary.

It is a further preferred object of the present invention to provide a means of safe hygienic handling of waste fluid by efficiently draining fluid through a closed system into a detachable and resealable waste receptacle, without the risk of blockage.

According to the invention there is provided a device for rectal lavage, comprising:

a generally rigid tubular body having a relatively flexible tapered front end nozzle portion for insertion into the anus of a patient;

a port for the insertion of an irrigation hose into the device;

an opening in the nozzle for the passage of the irrigation hose there-through;

at least one drain hole positioned in the nozzle, spaced from the opening, for the passage of irrigated fecal matter from the rectum into the hollow interior of the tubular body; and a discharge outlet from the hollow interior of the tubular body tube for the discharge of irrigated fecal matter from the device.

Preferably a plurality of the drain holes, such as from 4 to 6, are provided, which may be spaced about the axis of the tubular body.

Preferably the port is located at the rear end of the tubular body, on or adjacent the axis of the tubular body.

The nozzle opening preferably lies on the axis of the tubular body.

The port is preferably substantially in straight line relationship with the nozzle opening, i.e. an uninterrupted straight line path may be drawn from the port to the nozzle opening. This enables the hose to be more easily advanced through the device in use, without any bends or tarns.

Either or both of the port and the nozzle opening may have a circular cross-section, the diameter of the port preferably being not greater than the diameter of the nozzle opening. Thereby the irrigation hose will be a looser fit through the nozzle opening than through the port, this arrangement facilitating the advancement of the irrigation hose through the device.

The hollow interior of the tubular body defines a pathway between the drain hole(s) in the tapered nozzle and the discharge outlet. The port should preferably have a free internal dimension less than the minimum cross-sectional dimension of the pathway, to enable the irrigation hose to pass freely along the pathway from the port to the nozzle outlet, without impeding the flow of irrigated fecal matter from the drain holes to the discharge outlet. In an alternative embodiment, more complicated in terms of construction, two pathways are defined in the tubular body, the first leading from the port to the nozzle opening for the passage of the irrigation hose and the other passing from the drain hole(s) to the discharge outlet for the passage of irrigated fecal matter.

At least the rearward portion of the tubular member is formed of transparent material, to enable the user to see the fluid draining away.

Guide surfaces may be provided within the tubular body, especially within the nozzle, to guide the irrigation hose from the port to the nozzle opening. The guide surfaces may be formed by internal ribbing leading to the nozzle opening.

The discharge outlet is preferably formed as a side tube. In one embodiment, the side tube may be shaped to constitute a hand grip (i.e. have a surface configured with grooves to accommodate the fingers of a gripping hard), to ease control of the device by the operator.

The internal cross-section of the discharge outlet should be sufficient to avoid blocking by the irrigated fecal matter. In a preferred embodiment the internal cross-sectional area of the discharge outlet is greater than the internal cross-sectional area of the largest of the drain hole(s).

The device will usually have a discharge cube connected to the discharge outlet, the discharge tube preferably being deformable and external clamping means being provided to enable the discharge tube to be closed. Such a closable discharge cube connected to the discharge outlet enables the operator to selectively close the discharge tube to retain the irrigation fluid inside the patient.

The discharge tube may be connected to a resealable and detachable container. This enables the container, when full, to be disposed of in a convenient manner, or transported to an alternative location for treatment and/or analysis of its contents.

The container preferably includes a threaded spigot onto which an end piece of the discharge tube is screwed and a closure cap is provided to be screwed onto the threaded spigot to seal the container when the latter is full. The capacity of the container is typically from about 3 to about 10 l. The container is preferably collapsible and expandable and formed of flexible material. The construction of the container can be chosen such that, when full, it is of a size and weight which can be easily disposed of safely.

The tubular body is preferably formed of a medical grade material such as ABS or TPE and may be manufactured by injection molding or dip molding. The nozzle, port and discharge outlet are usefully formed as an integral entity with the tubular body, but the requirement for the nozzle to be more flexible than the rearward portion of the tubular body means that forming a separate nozzle to be bonded to the more rigid rearward portion of the tubular body is preferred. The nozzle is more flexible, i.e. pliable to enable atraumatic insertion.

The invention is also directed to the combination of the device with an irrigation hose which is a sliding fit through the port and through the nozzle opening. Preferably the irrigation hose is a sealing fit through the port. When the port incorporates a seal, the seal may be formed as an integral membrane with an axial hole having a free internal diameter less than the outer diameter of the irrigation tube.

The irrigation hose will have a length exceeding the distance from the port to the nozzle opening, ideally having a length which is considerably longer than the device to enable the hose to be advanced as required through the rectum of the patient, while continuing to be connected to the irrigation fluid source. The hose may be advanced through the device by hand or by mechanical means. To assist the advance of the hose through the port it is preferred to form the hose, the port and the walls of the nozzle opening from low-friction material, or to coat these members with such a material.

Furthermore, the invention is also directed to a method for rectal irrigation by the use of the device, wherein the device is inserted into the anus of the patient, the irrigation hose is fed through the device into the rectum of the patient, irrigation fluid is passed through the irrigation hose and irrigated fecal matter is allowed to pass through the drain holes into the hollow interior of the tubular body and is discharged therefrom through the discharge outlet.

The irrigation hose may continue to be advanced through the device as irrigation continues thereby to advance the forward end of the irrigation hose into the colon of the patient.

The irrigation fluid will normally be a liquid, although the device is suitable for use with compressed air, or a mixture of air and liquid. A suitable liquid is water, or saline solution and may comprise a topical preparation, to clean the site following tumor removal.

The method may be carried out as part of a bowel surgical operation.

The invention will now be further described, purely by way of example, with reference to the accompanying drawings, in which.

Figure 1:
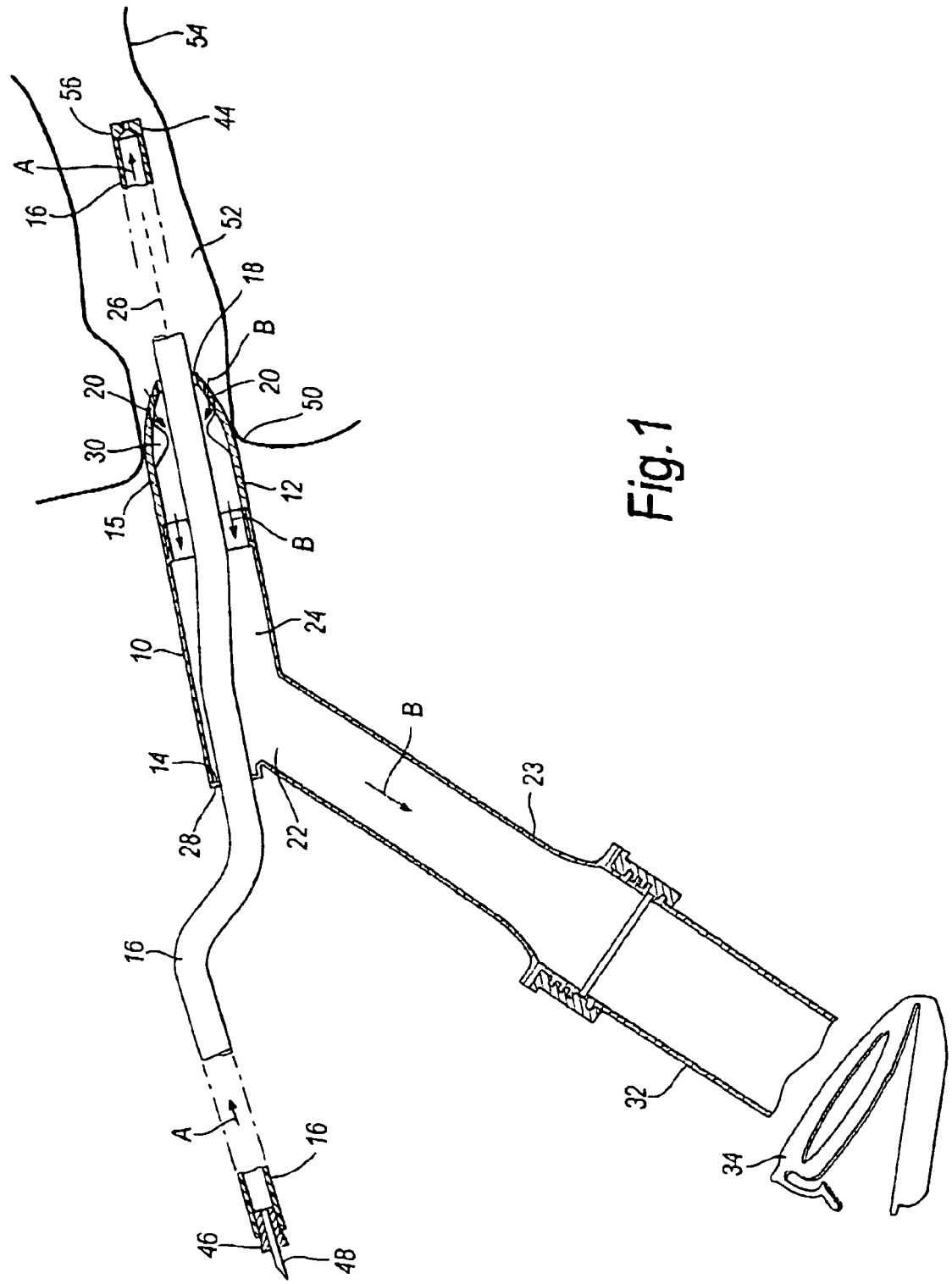
FIG. 1 shows, partly in cross-section, a rectal lavage device according to the invention.
Figure 2:
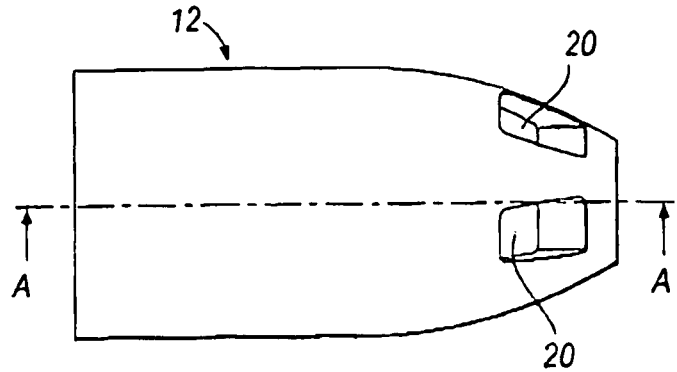
FIG. 2 shows the nozzle of the device shown in FIG. 1.
Figure 3:
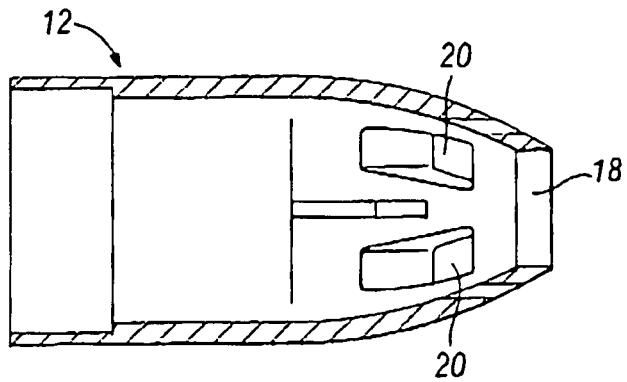
FIG. 3 shows a cross-section of the nozzle taken on the line A-A of FIG. 2.
Figure 4:
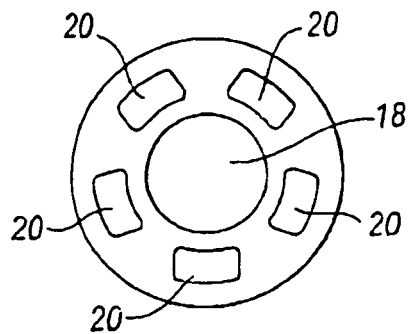
FIG. 4 is a front end view of the nozzle shown in FIG. 2.
Figure 5:
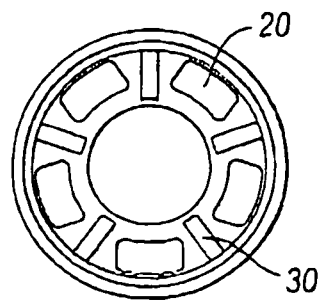
FIG. 5 is a rear end view of the nozzle shown in FIG. 2.

The rectal lavage device includes a tubular body 10 formed by injection molding having a generally rigid rearward portion 11 having a diameter of about 26.0 mm formed of transparent medical grade ABS and a relatively flexible tapered front end nozzle 12 portion formed of a partially transparent thermoplastic elastomeric material for insertion into the anus 50 of a patient.

The tubular body 10 is formed of a length of about 53.6 mm and a diameter of about 26.0 mm having a thickness of 2 to 3 mm. A port 14 having a circular cross-section of about 14.0 mm is located at the rear end 28 of the tubular body 10 for the insertion of an irrigation hose 16 formed of a medical grade PVC into the device. The hose 16 having an integrally formed tip 56 at its forward end 44 to increase irrigation fluid pressure and protect the inside of the rectum, while at its other end it carries an insert 46 incorporating a spike 48, for connection to a standard saline supply bag (not shown).

There is an opening 18 in the nozzle 12 for the passage of the irrigation hose 16 there-through. The nozzle opening 18 has a circular cross-section of about 11.0 mm diameter and lies on the axis 26 of the tubular body 10. The diameter of the nozzle opening 18 is slightly greater than the diameter of the port 14, so that the irrigation hose 16 is a sliding fit through the port 14 and through the nozzle opening 18. In a possible embodiment, the irrigation hose 16 is a sealing fit through the port 14.

Five drain holes 20 having dimensions of about 6.0 mm by 3.0 mm are positioned in the nozzle 12, forward of the broadest region 15 of the nozzle 12. The drain holes 20 are spaced about the axis 26 of the tubular body 10 and spaced from the opening 18, for the passage of irrigated fecal matter from the rectum 52 into the hollow interior 24 of the tubular body 10.

Guide surfaces in the form of internal ribbing 30 are provided within the nozzle 12 leading to the nozzle opening 18 to guide the irrigation hose 16 from the port 14 to the nozzle opening 18.

A discharge outlet 22 leads from the hollow interior 24 of the tubular body 10 into a sidearm 23 having an effective diameter of about 26 mm and a length of about 121.2 mm for the discharge of irrigated fecal matter from the device. A lay-flat PVC discharge tube 32 having a diameter of about 30 mm is connected to the side arm 23. The discharge cube 32 is deformable and an external clamp 34 is provided to enable the discharge cube 32 to be closed.

Figure 6:
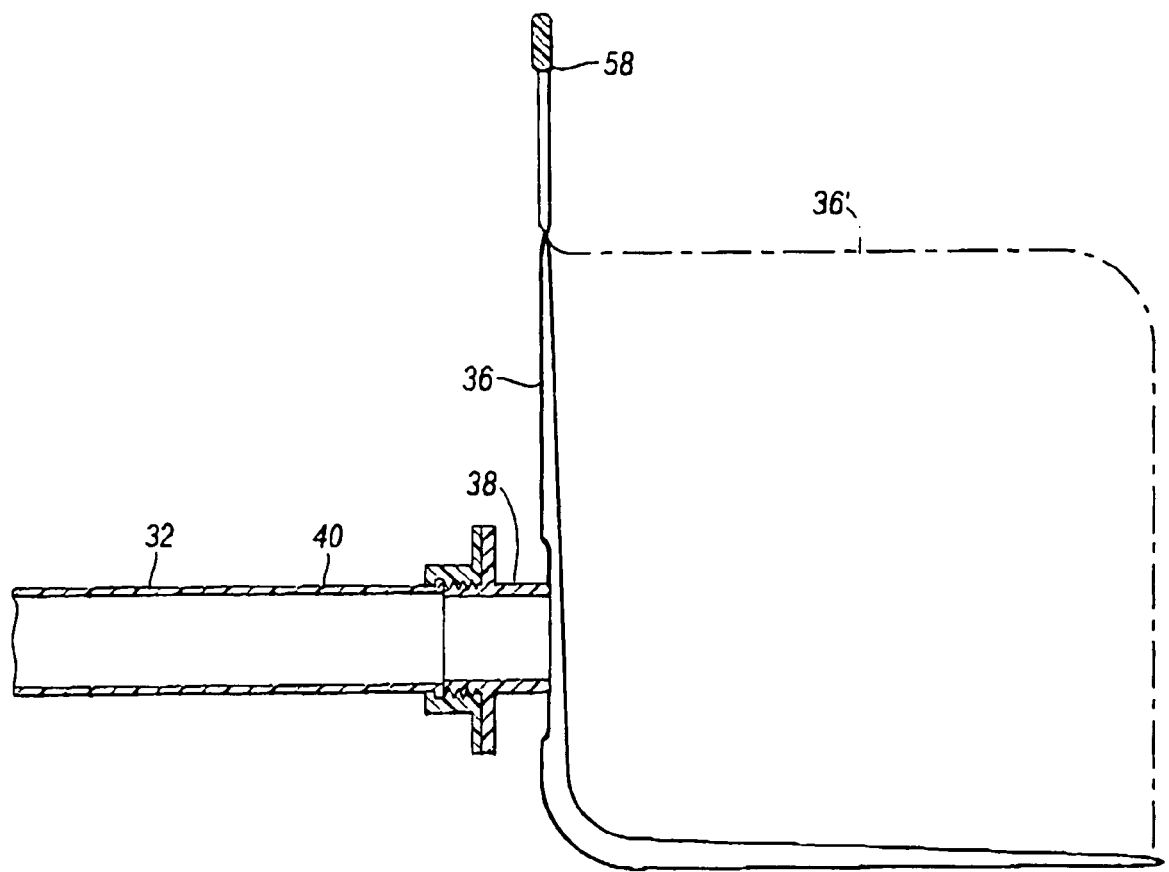
FIG. 6 shows a container for use with the device shown in FIG. 1, in a collapsed condition.

The discharge cube 32 is connected to resealable and detachable container 36 (see FIG. 6). The container 36 is collapsible and expandable and formed of flexible material. The container 36 includes a threaded spigot 38 onto which an end piece 40 of the discharge tube 32 is screwed and a closure cap 42 (see FIG. 7) is provided to be screwed onto the threaded spigot 38 to seal the container 36 when the latter is full with waste material 43.

The device is used for rectal irrigation for example as part of a bowel surgical operation, as follows.

After applying a lubricant such as KY-jelly (Trade Mark), ex. Johnson & Johnson, to the nozzle and/or to the patient, the device is inserted into the anus 50 of the patient. The irrigation hose 16 is then fed through the device into the rectum 52 of the patient and irrigation fluid, for example a saline solution, is passed through the irrigation hose 16. Irrigated fecal matter is allowed to pass through the drain holes 20 into the hollow interior 24 of the tubular body 10 and is discharged therefrom through the discharge outlet 22.

The saline solution is passed under gravity through the hose 16, as shown by the arrows A, to cleanse fecal matter from the rectum. Although not shown in the drawings, a clamp or other controllable closing device may be provided at a convenient position along the length of the hose 16, upstream of the device, to enable the operator to control the rate of flow of saline into the rectum.

Cleansed fecal matter returns to the tubular body 10 to be discharged through the discharge outlet 22, as shown by the arrows B. Optionally, the hose 16 continues to be advanced by hand through the device further into the rectum as fecal matter is cleansed therefrom thereby to advance the forward end 44 of the irrigation hose 16 into the colon 54 of the patient. The clear construction of the discharge tube 32 enables the operator to see the returning liquid.

The closable discharge tube 32 connected to the discharge outlet 22, is selectively closed to retain the irrigation fluid inside the patient.

It the device is being used following the removal of a tumor, following irrigation, the saline solution may be replaced with an aqueous topical preparation to clean the sire.

Figure 7:
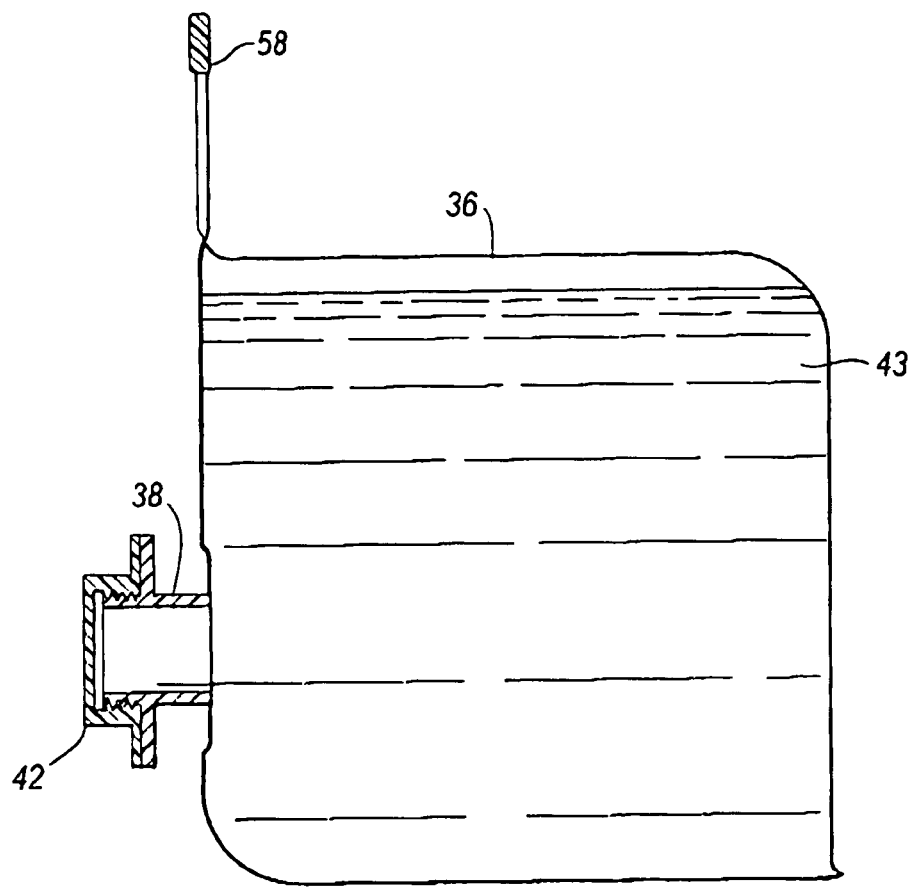
FIG. 7 shows the container in a filled and sealed condition.

As shown in FIGS. 6 and 7, the container 36 is formed of flexible polyethylene and is as to be able to adopt the collapsed configuration shown in heavy lines, while being expandable to the configuration shown in broken lines 36'. In the expanded condition (see FIG. 7), the container 26 has a volume of about 3 l. The container is optionally provided with a carrying handle 58. When the container 36 is full, the discharge tube 32 can be removed therefrom and replaced by the closure cap 42. The full container can then be disposed of, or transported for treatment and/or analysis of its contents, in a convenient manner.

The invention claimed is:

1. A device for rectal lavage, comprising:
 a rigid tubular body (10);
 a nozzle (12) for insertion into the anus (50) of a patient, the nozzle (12) being constituted by a tapered front end portion of the tubular body (10) that is more flexible than said rigid tubular body, and having a broadest region (15);
 a port (14) for the insertion of an irrigation hose (16) into the device;
 an opening (18) in said nozzle (12) for the passage of the irrigation hose (16) there-through;
 at least one drain hole (20) positioned in said nozzle (12), forward of said broadest region (15) thereof and spaced from said opening (18), for the passage of irrigated fecal matter from the rectum (52) into the hollow interior (24) of said tubular body (10); and
 a discharge outlet (22) from the hollow interior (24) of said tubular body (10) for the discharge of irrigated fecal matter from the device, the internal cross-sectional area of the discharge outlet being greater than the internal cross-sectional area of the largest of the drain hole(s).

2. The device of claim 1, wherein a plurality of said drain holes (20) are provided.

3. The device of claim 2, wherein said plurality of drain holes (20) are spaced about the axis (26) of said tubular body (10).

4. The device of claim 1, wherein said port (14) is located at the rear end (28) of said tubular body (10).

5. The device of claim 1, wherein said nozzle (12) is formed as a separate member from the rearward portion (11) of said tubular body and is bonded thereto.

6. The device of claim 1, wherein said nozzle opening (18) lies on the axis (26) of said tubular body (10).

7. The device of claim 1, wherein said port (14) has a circular cross section.

8. The device of claim 1, wherein said nozzle opening (18) has a circular cross section.

9. The device of claim 1, wherein said port (14) has a circular cross section, said nozzle opening (18) has a circular cross section and the diameter of said port (14) is not greater than the diameter of said nozzle opening (18).

10. The device of claim 1, wherein at least said nozzle (12) is formed of transparent material.

11. The device of claim 1, wherein guide surfaces (30) are provided within the tubular body (10) to guide the irrigation hose (16) from said port (14) to said nozzle opening (18).

12. The device of claim 11, wherein said guide surfaces are formed by internal ribbing (30) leading to said nozzle opening (18).

13. The device of claim 1, having a discharge tube (32) connected to said discharge outlet (22) and wherein said discharge tube (32) is deformable and external clamping means (34) are provided to enable the discharge tube (32) to be closed.

14. The device of claim 13, wherein said discharge tube (32) is connected to a resealable and detachable container (36).

15. The device of claim 13, wherein said discharge tube (32) has a lay-flat configuration.

16. The device of claim 14, wherein said container (36) includes a threaded spigot (38) onto which an end piece (40) of said discharge tube (32) is screwed and a closure cap (42) is provided to be screwed onto said threaded spigot (38) to seal the container (36) when the latter is full.

17. The device of claim 14, wherein the container (36) is collapsible and expandable and formed of flexible material.

18. The combination of the device of claim 1 with an irrigation hose (16) which is a sliding fit through said port (14) and through said nozzle opening (18).

19. The combination of claim 18, wherein said irrigation hose (16) is a sealing fit through said port (14).

20. A method for rectal irrigation by the use of the combination of the device of claim 1 with an irrigation hose (16) which is a sliding fit through said port (14) and through said nozzle opening (18), wherein the device is inserted into the anus (50) of the patient, the irrigation hose (16) is fed through the device into the rectum (52) of the patient and irrigation fluid is passed through the irrigation hose (16) and irrigated fecal matter is allowed to pass through said drain holes (20) into the hollow interior (24) of said tubular body (10) and is discharged therefrom through said discharge outlet (22).

21. The method of claim 20, wherein said irrigation hose (16) continues to be advanced through the device as irrigation continues thereby to advance the forward end (44) of said irrigation hose (16) into the colon (54) of the patient.

22. The method of claim 20, wherein said irrigation fluid comprises a topical preparation to clean the site following removal of a tumor.

23. The method of claim 20, carried out as part of a bowel surgical operation.

24. The method of claim 20, wherein a closable discharge tube (32) is connected to said discharge outlet (22), and is selectively closed to retain the irrigation fluid inside the patient.

25. The device of claim 1, wherein said tubular body has a rearward portion, and wherein at least said rearward portion of said tubular body is formed of transparent material.

26. A device for rectal lavage, comprising:
   a rigid tubular body (10) having a hollow interior;
   a nozzle (12) for insertion into the anus (50) of a patient, the nozzle (12) being constituted by a relatively flexible tapered front end portion of the tubular body (10) and having a broadest region (15);
   a port (14) for the insertion of an irrigation hose (16) into the device;
   an irrigation hose (16) positioned in said hollow interior of said rigid tubular body (10);
   an opening (18) in said nozzle (12) for the passage of the irrigation hose (16) there-through;
   at least one drain hole (20) positioned in said nozzle (12), forward of said broadest region (15) thereof and spaced from said opening (18), for the passage of irrigated fecal matter from the rectum (52) into said hollow interior (24) of said tubular body (10) about said irrigation hose; and
   a discharge outlet (22) from said hollow interior (24) of said tubular body (10) for the discharge of irrigated fecal matter from the device, the internal cross-sectional area of the discharge outlet being greater than the internal cross-sectional area of the largest of the drain hole(s).

* * * * *